United States Patent
Call et al.

(10) Patent No.: US 11,504,517 B2
(45) Date of Patent: Nov. 22, 2022

(54) FLUID LINE CONNECTOR DEVICES METHODS AND SYSTEMS

(71) Applicant: NxStage Medical, Inc., Lawrence, MA (US)

(72) Inventors: Daniel Call, Chicago, IL (US); Matthew Onken, Acton, MA (US)

(73) Assignee: NxStage Medical, Inc., Lawrence, MA (US)

( * ) Notice: Subject to any disclaimer, the term of this patent is extended or adjusted under 35 U.S.C. 154(b) by 692 days.

(21) Appl. No.: 16/060,855

(22) PCT Filed: Dec. 9, 2016

(86) PCT No.: PCT/US2016/065894
§ 371 (c)(1),
(2) Date: Jun. 8, 2018

(87) PCT Pub. No.: WO2017/100621
PCT Pub. Date: Jun. 15, 2017

(65) Prior Publication Data
US 2019/0001113 A1    Jan. 3, 2019

Related U.S. Application Data

(60) Provisional application No. 62/266,553, filed on Dec. 11, 2015.

(51) Int. Cl.
*A61M 39/10* (2006.01)
*A61M 1/14* (2006.01)
(Continued)

(52) U.S. Cl.
CPC .......... *A61M 39/1011* (2013.01); *A61M 1/14* (2013.01); *A61M 1/367* (2013.01);
(Continued)

(58) Field of Classification Search
CPC ........ A61M 1/14; A61M 1/28; A61M 39/221; A61M 39/1011; A61M 2205/273; A61M 2039/1061; A61M 2039/1077
See application file for complete search history.

(56) References Cited

U.S. PATENT DOCUMENTS 4,121,585 A   10/1978   Becker
4,230,109 A   10/1980   Geiss
(Continued)

FOREIGN PATENT DOCUMENTS

CN   201150709 Y   11/2008
DE   60013965      3/2006
(Continued)

OTHER PUBLICATIONS

NxStageCriticalCare, ChangingTherapyFluidBags.wmv, Nov. 2, 2010, Youtube, https://www.youtube.com/watch?v=Aho-0zc5sXE (Year: 2010).*

(Continued)

*Primary Examiner* — Rebecca E Eisenberg
*Assistant Examiner* — Anna E Goldberg-Richmeier
(74) *Attorney, Agent, or Firm* — Potomac Law Group, PLLC; George S. Dolina (57) ABSTRACT

A frangible connector has a first side that forms a female luer when a second side is fractured at a predefined break line. The second side may be connected to a fluid circuit, for example, a source of medical treatment fluid such as dialysate.

8 Claims, 6 Drawing Sheets (51) Int. Cl.
*A61M 1/36* (2006.01)
*A61M 25/00* (2006.01)

(52) U.S. Cl.
CPC ............ *A61M 25/00* (2013.01); *A61M 39/10* (2013.01); *A61M 2039/1033* (2013.01); *A61M 2039/1061* (2013.01)

(56) References Cited

U.S. PATENT DOCUMENTS

| | | |
|---|---|---|
| 4,396,382 A | 8/1983 | Goldhaber |
| 4,439,188 A | 3/1984 | Dennehey et al. |
| 4,512,764 A | 4/1985 | Wunsch |
| 4,585,435 A | 4/1986 | Vaillancourt |
| 4,585,436 A | 4/1986 | Davis et al. |
| 4,617,012 A | 10/1986 | Vaillancourt |
| 4,617,161 A | 10/1986 | Rollins et al. |
| 4,639,019 A | 1/1987 | Mittleman |
| 4,724,900 A | 2/1988 | Baurmeister et al. |
| 4,745,950 A | 5/1988 | Mathieu |
| 4,826,486 A | 5/1989 | Palsrok et al. |
| 4,834,706 A | 5/1989 | Beck et al. |
| 4,950,255 A | 8/1990 | Brown et al. |
| 4,997,577 A | 3/1991 | Stewart |
| 5,004,535 A | 4/1991 | Bosko et al. |
| 5,061,365 A | 10/1991 | Utterberg |
| 5,139,483 A | 8/1992 | Ryan |
| 5,163,922 A | 11/1992 | McElveen et al. |
| 5,201,725 A | 4/1993 | Kling |
| 5,221,267 A | 6/1993 | Folden |
| 5,242,425 A | 9/1993 | White et al. |
| 5,259,843 A * | 11/1993 | Watanabe ............. A61M 39/00 128/912 |
| 5,275,724 A | 1/1994 | Bucchianeri et al. |
| 5,279,605 A | 1/1994 | Karrasch et al. |
| 5,292,308 A | 3/1994 | Ryan |
| 5,303,751 A | 4/1994 | Slater et al. |
| 5,336,173 A | 8/1994 | Folden |
| 5,350,201 A | 9/1994 | Bynum |
| 5,372,392 A | 12/1994 | Dunn et al. |
| 5,431,496 A | 7/1995 | Balteau et al. |
| 5,437,624 A | 8/1995 | Langley |
| 5,484,397 A | 1/1996 | Twardowski |
| 5,584,813 A | 12/1996 | Livingston et al. |
| 5,690,614 A | 11/1997 | Carr et al. |
| 5,762,789 A | 6/1998 | Reyes et al. |
| 5,783,072 A | 7/1998 | Kenley et al. |
| 5,792,425 A | 8/1998 | Clark et al. |
| 5,836,933 A | 11/1998 | Buttitta et al. |
| 5,843,309 A | 12/1998 | Mancil |
| 5,871,500 A | 2/1999 | Jepson et al. |
| 5,938,622 A | 8/1999 | Chen |
| 5,957,894 A | 9/1999 | Kerwin et al. |
| 5,965,086 A | 10/1999 | Rose et al. |
| 5,988,700 A | 11/1999 | Prichard |
| 6,003,556 A | 12/1999 | Brugger et al. |
| 6,004,311 A | 12/1999 | Heilmann et al. |
| 6,050,285 A | 4/2000 | Goncze et al. |
| 6,056,015 A | 5/2000 | Lewis |
| 6,068,770 A | 5/2000 | Niermeyer et al. |
| 6,120,490 A | 9/2000 | Neftel |
| 6,142,938 A | 11/2000 | Satherley |
| 6,146,354 A | 11/2000 | Beil |
| 6,171,484 B1 | 1/2001 | Schnell et al. |
| 6,315,707 B1 | 11/2001 | Smith et al. |
| 6,322,551 B1 | 11/2001 | Brugger |
| 6,387,069 B1 | 5/2002 | Utterberg |
| 6,485,483 B1 | 11/2002 | Fujii |
| 6,488,650 B1 | 12/2002 | Epstein et al. |
| 6,502,604 B1 | 1/2003 | Lewis |
| 6,565,806 B1 | 5/2003 | Grimm |
| 6,572,155 B2 | 6/2003 | Dehmer |
| 6,585,703 B1 | 7/2003 | Kassel et al. |
| 6,613,016 B1 | 9/2003 | Ku |
| 6,623,455 B2 | 9/2003 | Small et al. |
| 6,635,179 B1 | 10/2003 | Summerton et al. |
| 6,685,677 B2 | 2/2004 | Green |
| 6,696,018 B2 | 2/2004 | Buchanan |
| 6,712,963 B2 | 3/2004 | Schick |
| 6,719,907 B2 | 4/2004 | Collins et al. |
| 6,843,513 B2 | 1/2005 | Guala |
| 6,893,056 B2 | 5/2005 | Guala |
| 6,911,014 B2 | 6/2005 | Wentling et al. |
| 6,945,969 B1 | 9/2005 | Morris et al. |
| 7,017,948 B2 | 3/2006 | Sunohara et al. |
| 7,052,606 B2 | 5/2006 | Gibbs et al. |
| 7,070,589 B2 | 7/2006 | Lolachi et al. |
| 7,077,284 B2 | 7/2006 | Ritter |
| 7,135,008 B2 | 11/2006 | O'Mahony et al. |
| 7,138,045 B2 | 11/2006 | Sferrazza |
| 7,141,097 B2 | 11/2006 | Leahey |
| 7,147,620 B2 | 12/2006 | Kessler et al. |
| 7,247,153 B2 | 7/2007 | Guala |
| 7,252,308 B2 | 8/2007 | Thilly |
| 7,316,662 B2 | 1/2008 | Delnevo et al. |
| 7,351,218 B2 | 4/2008 | Bene |
| 7,507,226 B2 | 3/2009 | Stanus et al. |
| 7,588,692 B2 | 9/2009 | Antwiler et al. |
| 7,635,343 B2 | 12/2009 | McIntosh et al. |
| 7,641,753 B2 | 1/2010 | Gao et al. |
| 7,648,494 B2 | 1/2010 | Kornerup et al. |
| 7,686,279 B2 | 3/2010 | Nerbonne et al. |
| 7,686,779 B1 | 3/2010 | Gibbs |
| 7,758,082 B2 | 7/2010 | Weigel et al. |
| 7,766,394 B2 | 8/2010 | Sage et al. |
| 7,789,245 B2 | 9/2010 | Westberg et al. |
| 7,806,737 B2 | 10/2010 | Mark et al. |
| 7,857,802 B2 | 12/2010 | Brandenburger et al. |
| 7,892,428 B2 | 2/2011 | Ardans et al. |
| 7,935,258 B2 | 5/2011 | Rovatti et al. |
| 7,951,121 B2 | 5/2011 | Weaver et al. |
| 8,012,126 B2 | 9/2011 | Tipsmark et al. |
| 8,021,319 B2 | 9/2011 | Delnevo et al. |
| 8,021,334 B2 | 9/2011 | Shekalim |
| 8,042,838 B2 | 10/2011 | Buckler et al. |
| 8,074,964 B2 | 12/2011 | Mansour et al. |
| 8,088,099 B2 | 1/2012 | McIntosh et al. |
| 8,152,116 B2 | 4/2012 | Westberg |
| 8,163,064 B2 | 4/2012 | Bredesen et al. |
| 8,172,823 B2 | 5/2012 | Rondeau et al. |
| 8,177,771 B2 | 5/2012 | Butts et al. |
| 8,182,686 B2 | 5/2012 | Witthaus et al. |
| 8,210,049 B2 | 7/2012 | Brugger |
| 8,333,724 B2 | 12/2012 | Barrett et al. |
| 8,431,086 B2 | 4/2013 | Lurvey et al. |
| 8,454,573 B2 | 6/2013 | Wyatt et al. |
| 8,469,331 B2 * | 6/2013 | Burbank ............. A61M 1/1656 251/4 |
| 8,469,931 B2 | 6/2013 | Tryggvason et al. |
| 8,508,368 B2 | 8/2013 | Potyrailo et al. |
| 8,511,638 B2 | 8/2013 | Mansour et al. |
| 8,512,553 B2 | 8/2013 | Cicchello et al. |
| 8,562,908 B2 | 10/2013 | Kenley |
| 8,596,326 B2 | 12/2013 | Loy |
| 8,622,893 B2 | 1/2014 | Mathieu |
| 8,622,986 B2 | 1/2014 | Ramella et al. |
| 8,647,326 B2 | 2/2014 | Solomon et al. |
| 8,738,151 B2 | 5/2014 | Nelson |
| 8,771,513 B2 | 7/2014 | Heinrich et al. |
| 8,858,485 B2 | 10/2014 | Neri et al. |
| 8,944,082 B2 | 2/2015 | Cairns |
| 8,945,036 B2 | 2/2015 | Szamosfalvi et al. |
| 8,968,238 B2 | 3/2015 | Page et al. |
| 9,057,469 B2 | 6/2015 | Wei |
| 9,089,682 B2 | 7/2015 | Yeh et al. |
| 9,101,473 B2 | 8/2015 | Sweeney et al. |
| 9,119,947 B2 | 9/2015 | Tsao |
| 9,145,995 B2 | 9/2015 | Gastauer et al. |
| 9,198,581 B2 | 12/2015 | Eberle et al. |
| 9,211,075 B2 | 12/2015 | Quintanar et al. |
| 9,283,372 B2 | 3/2016 | Bondhus et al. |
| 9,339,605 B2 | 5/2016 | Wimpenny et al. |
| 9,345,828 B2 | 5/2016 | Browne |
| 9,364,652 B2 | 6/2016 | Griffith et al. |
| 9,370,651 B2 | 6/2016 | Zollinger et al. |

(56) References Cited

U.S. PATENT DOCUMENTS

| | | | |
|---|---|---|---|
| 9,393,398 | B2 | 7/2016 | Truitt et al. |
| 9,408,971 | B2 | 8/2016 | Carlyon |
| 9,532,742 | B2 | 1/2017 | Sim et al. |
| 9,629,950 | B2 | 4/2017 | Park et al. |
| 9,629,951 | B2 | 4/2017 | Delmage et al. |
| 9,636,493 | B2 | 5/2017 | Chung |
| 9,669,163 | B2 | 6/2017 | McNall et al. |
| 9,687,645 | B2 | 6/2017 | Wesseler |
| 9,694,139 | B2 | 7/2017 | Shaw et al. |
| 9,772,246 | B2 | 9/2017 | Hoffman et al. |
| 2002/0043051 | A1 | 4/2002 | Manica et al. |
| 2003/0010717 | A1 | 1/2003 | Brugger et al. |
| 2003/0074862 | A1 | 4/2003 | Lohmuller |
| 2003/0187420 | A1 | 10/2003 | Akerlund et al. |
| 2004/0009542 | A1 | 1/2004 | Dumont et al. |
| 2004/0045890 | A1 | 3/2004 | Herczeg |
| 2004/0067161 | A1* | 4/2004 | Axelsson ............ A61M 1/288 422/44 |
| 2005/0082210 | A1 | 4/2005 | Favre |
| 2005/0085762 | A1 | 4/2005 | Vijay et al. |
| 2006/0035494 | A1 | 2/2006 | Sugaya et al. |
| 2006/0272997 | A1 | 12/2006 | Liu |
| 2007/0073237 | A1 | 3/2007 | Rodd |
| 2007/0073245 | A1 | 3/2007 | Shih |
| 2007/0131610 | A1 | 6/2007 | Peng et al. |
| 2007/0173758 | A1 | 7/2007 | Chen |
| 2007/0197922 | A1 | 8/2007 | Bradley et al. |
| 2007/0261214 | A1 | 11/2007 | Nerbonne et al. |
| 2008/0077050 | A1 | 3/2008 | Malmborg et al. |
| 2008/0103476 | A1 | 5/2008 | Schulte |
| 2008/0132876 | A1 | 6/2008 | Felt |
| 2008/0139909 | A1 | 6/2008 | Corl et al. |
| 2008/0147012 | A1 | 6/2008 | Rome |
| 2009/0198170 | A1* | 8/2009 | Childers ............ A61M 1/1601 604/6.09 |
| 2009/0204080 | A1 | 8/2009 | Balteau et al. |
| 2009/0306621 | A1 | 12/2009 | Thome et al. |
| 2010/0152640 | A1 | 6/2010 | Golding et al. |
| 2011/0060328 | A1 | 3/2011 | Skwarek et al. |
| 2011/0226256 | A1 | 9/2011 | Dubach |
| 2012/0029333 | A1 | 2/2012 | Dogwiler et al. |
| 2012/0047623 | A1 | 3/2012 | Oudenallen et al. |
| 2012/0116321 | A1 | 5/2012 | Brugger |
| 2012/0175806 | A1 | 7/2012 | Delano |
| 2013/0165851 | A1 | 6/2013 | Geiger et al. |
| 2013/0237830 | A1 | 9/2013 | Warren et al. |
| 2013/0264821 | A1 | 10/2013 | Duck et al. |
| 2014/0008366 | A1 | 1/2014 | Genosar |
| 2014/0076483 | A1 | 3/2014 | Pirie et al. |
| 2014/0144794 | A1 | 5/2014 | Eyrard et al. |
| 2014/0187892 | A1 | 7/2014 | Gupta et al. |
| 2014/0238909 | A1 | 8/2014 | Brugger et al. |
| 2014/0296745 | A1 | 10/2014 | Cash |
| 2014/0306447 | A1 | 10/2014 | Werth |
| 2014/0318995 | A1 | 10/2014 | Eilertsen |
| 2014/0350485 | A1 | 11/2014 | Sonderegger et al. |
| 2014/0350486 | A1 | 11/2014 | Cordes |
| 2014/0371598 | A1 | 12/2014 | Okubo et al. |
| 2015/0034194 | A1* | 2/2015 | Uber, III ............ A61M 39/1011 137/797 |
| 2015/0093450 | A1 | 4/2015 | Riser et al. |
| 2015/0165185 | A1 | 6/2015 | Cohen et al. |
| 2015/0223671 | A1 | 8/2015 | Sung et al. |
| 2015/0238746 | A1 | 8/2015 | Nisipeanu et al. |
| 2015/0250945 | A1 | 9/2015 | Kim |
| 2015/0306372 | A1 | 10/2015 | Brault-Guyon et al. |
| 2016/0008224 | A1 | 1/2016 | Rahimy et al. |
| 2016/0015961 | A1 | 1/2016 | Mansour et al. |
| 2016/0101276 | A1 | 4/2016 | Tekeste |
| 2016/0113813 | A1 | 4/2016 | Lim et al. |
| 2016/0143811 | A1 | 5/2016 | Poncon et al. |
| 2016/0144118 | A1 | 5/2016 | Solomon et al. |
| 2016/0151573 | A1 | 6/2016 | Binninger |
| 2016/0158523 | A1 | 6/2016 | Helm |
| 2016/0175201 | A1 | 6/2016 | Schuessler |
| 2016/0199568 | A1 | 7/2016 | McNall et al. |
| 2016/0206868 | A1 | 7/2016 | Guala |
| 2016/0213441 | A1 | 7/2016 | Connolly |
| 2016/0220806 | A1 | 8/2016 | Mansour et al. |
| 2016/0317120 | A1 | 11/2016 | Elbert |
| 2016/0354288 | A1 | 12/2016 | Uehara et al. |
| 2017/0000979 | A1 | 1/2017 | Blacker |
| 2017/0203014 | A1 | 7/2017 | Kenley |

FOREIGN PATENT DOCUMENTS

| | | | |
|---|---|---|---|
| EP | 2275165 A2 | 1/2011 | |
| GB | 2538795 A | 11/2016 | |
| JP | 2001002127 A | 1/2001 | |
| JP | 3455701 B2 | 10/2003 | |
| JP | 4362036 B2 | 11/2009 | |
| JP | 5304073 B2 | 10/2013 | |
| JP | 5363928 B2 | 12/2013 | |
| RU | 2271834 C1 | 3/2006 | |
| WO | 02053211 A1 | 7/2002 | |
| WO | WO-02053211 A1 * | 7/2002 | ............ A61M 1/28 |
| WO | 2006083653 A2 | 8/2006 | |
| WO | 2014037110 A1 | 3/2014 | |

OTHER PUBLICATIONS

International Preliminary Report on Patentability for International Application No. PCT/US2016/065894 dated Jun. 21, 2018.

International Search Report and Written Opinion for International Application No. PCT/US2016/065894 dated Apr. 6, 2017.

Extended European Search Report dated Jun. 11, 2019 for European Patent Application No. 16873947.2.

\* cited by examiner

FLUID LINE CONNECTOR DEVICES METHODS AND SYSTEMS

CROSS-REFERENCE TO RELATED APPLICATIONS

This application is a U.S. national stage filing under 35 U.S.C. § 371 of International Application No. PCT/US2016/065894 filed Dec. 9, 2016, which claims the benefit of U.S. Provisional Application No. 62/266,553 filed Dec. 11, 2015, all of which are hereby incorporated by reference in their entireties.

BACKGROUND

The present invention relates to medical to fluid management systems and in particular embodiments, to fluid supply for renal replacement therapy. Renal failure is attended by physiological problems including water balance, minerals and the excretion metabolic waste, and others. Toxins such as urea, creatinine, and uric acid may accumulate in the blood and tissue compartments of patients. Dialysis treatments, including hemodialysis and dialysis removed excess water and toxins so as to replace the function of the kidneys. Dialysis may require a large volume of dialysate, for example about 50-120 liters may be required and consumed during one treatment session.

Dialysis helps restore the composition of the body's fluid environment to a more normal configuration. Dialysate composition are thus set to approximate the normal values in the body such that diffusion along favorable concentration gradients causes the concentrations of solutes that are initially abnormal are corrected. Certain electrolytes can be set at a nonphysiologic levels to achieve a more rapid correction. The dialysate can be individually adjusted to meet the specific needs of patients.

Fluids are used for priming a blood circuit of an extracorporeal fluid circuit and for treatment, for example as dialysate is consumed in dialysis treatments. There is a need to make connections and interchange connections in extracorporeal blood systems while maintaining sterility.

SUMMARY

A frangible connector has a first side that forms a female luer when a second side is fractured at a predefined break line. The second side may be connected to a fluid circuit, for example, a source of medical treatment fluid such as dialysate. By fracturing the frangible connector, the first side can be connected immediately to a different fluid circuit without undoing a connector. Further, the second side is not usable as a connector thereby preventing reconnection to a previously used fluid circuit. In embodiments, the second side is connected to an element that seals the fluid circuit to which it is attached. In embodiments, this seal is provided by a non-reopenable tubing clamp. In other embodiments, it can be provided with a cap. In still further embodiments, a self-sealing device such as a check valve may be provided to provide the seal. The second element with the non-reopenable tubing clamp may be provided as part of a fluid circuit such as a fluid circuit of a dialysis treatment system.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Figure 1A:
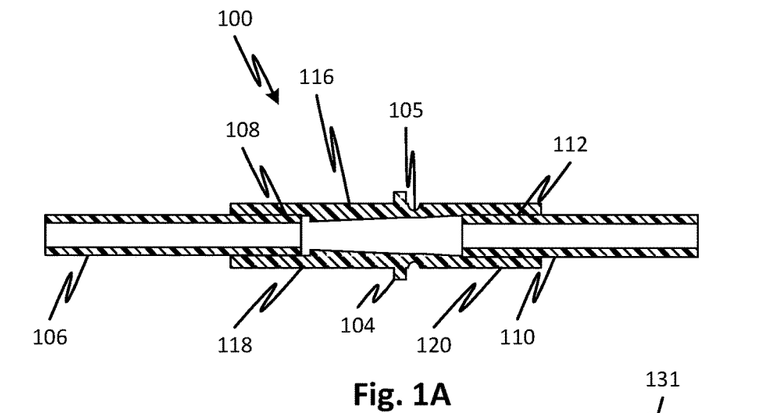
FIGS. 1A, 1B, and 1C show embodiments of a frangible connector with optional elements and showing the frangible connector prior to, and after, fracturing, according to embodiments of the disclosed subject matter.
Figure 1B:
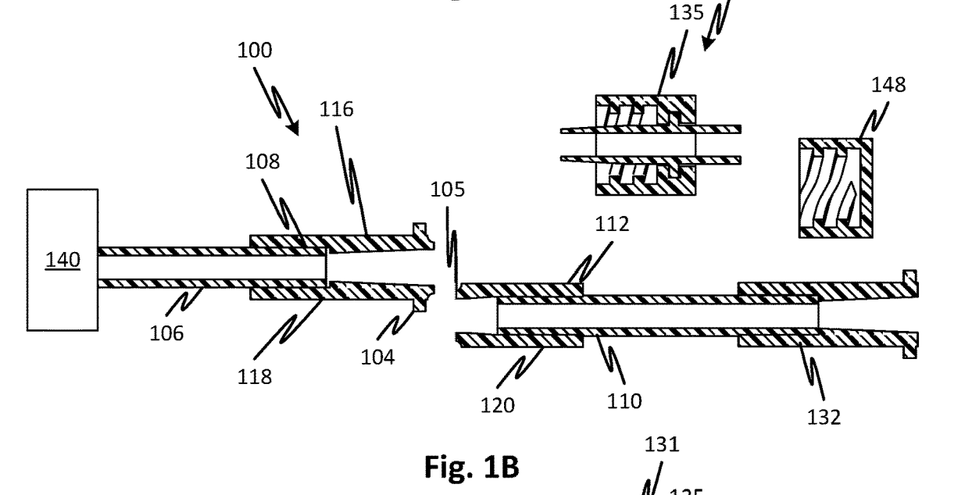
Figure 1C:
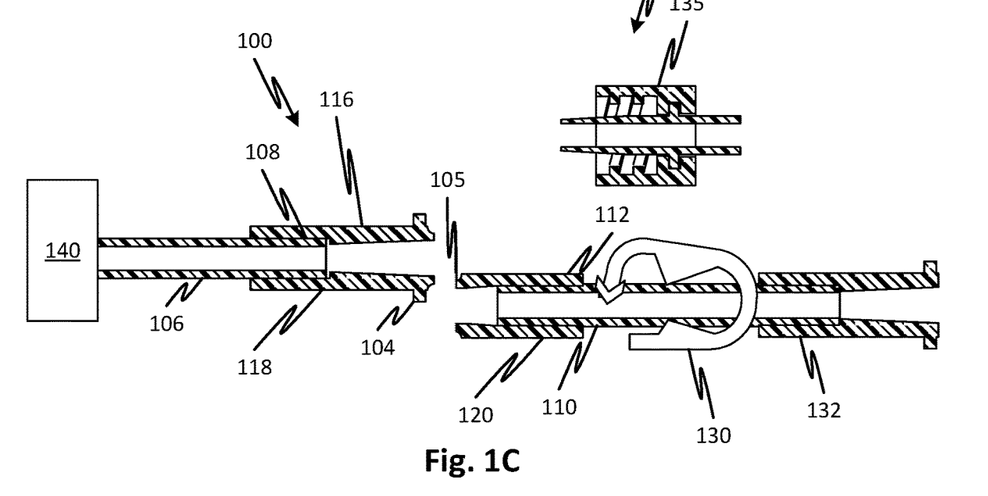

Referring to FIGS. 1A, 1B, and 1C, a frangible connector 100 has a first side 118 that forms a connector 116 when a frangible portion 105 is fractured separating the first side 118 from a second side 120 of the frangible connector 100. In the embodiment, the formed connector 116 is a female luer connector but could be any type of connector including a male luer connector. The frangible connector 100 second side 120 is left behind when the frangible portion 105 is fractured, thereby preventing further attachment to the second side 120. In embodiments, the second side 120 may form another connector of any type, for example a female luer formed by the second side 120 of the embodiment shown in FIG. 9. The frangible connector 100 may be connected at the first end to a tube 106, for example by solvent or thermal bonding to a recess 108 thereof. The tube 106 may be connected to a fluid circuit. The frangible connector 100 may be connected at the second end 120 to a further tube 110, for example by solvent or thermal bonding in a recess 112 thereof. The connector 116 may have external threads 104 which engage threads of a locking collar 135 of a complementary connector such as a male locking luer as shown at 131. The second side 120 of the frangible connector 100 can also be connected via tube 110 to a further connector 132 such as a female luer connector as shown at 132. The tube 106 may be permanently bonded to a fluid circuit 140 in further embodiments. For example, the assembly shown in FIG. 1B (before being fractured, as shown in FIGS. 1B and 1C) may be capped and sealed to protect the internal space of a fluid circuit.

The tube 110 may be further connected to a connector 132 such as a female luer connector. The connector 132 may be capped to seal the pre-connected fluid circuit 140 if present. The fluid circuit and frangible connector 100 components together with connector 132 and cap 148 may form a sealed deliverable element for a treatment system. A non-reopenable tubing clamp 130 may also be provided pre-attached to tube 110 to allow the frangible connector 100 second side 120 to be sealed and remain connected by the connector 132 to a further fluid handing device (not shown here) to seal the latter until the connector 132 is removed.

Figure 2:
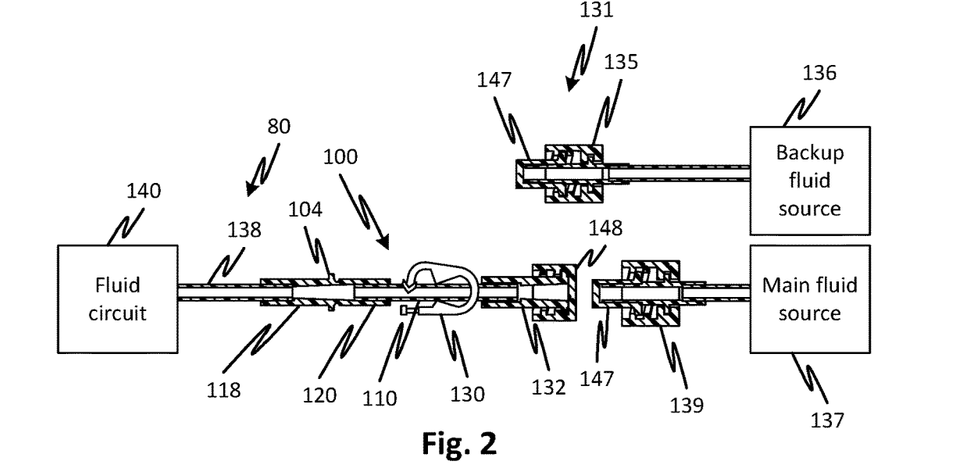
FIGS. 2-6 show the connector of FIGS. 1A, 1B, and 1C in a blood treatment implementation while illustrating a method of use, according to embodiments of the disclosed subject matter.

Referring now to FIG. 2, the frangible connector 100 is attached by a tube 138 (or other means) to form part of a sealed fluid circuit 80 assembly that includes a fluid circuit 140 such as a cartridge, a vessel, a network of tubing or other type of fluid management circuit for a treatment system, such as a dialysis system. The sealed fluid circuit assembly 80 has a connector 132 sealed by the cap 148 as described above. A main fluid source 137 may have a connector 139, in the embodiment, a male locking luer type connector. The latter is sealed by a cap 147. The main fluid source 137 may be an online or batch dialysate supply such as in a clinic or a home. The connector 139 may be configured to be connectable to connector 132 to supply fluid to the fluid circuit 140. In case of an interruption in the supply of fluid from the main fluid source 137, a backup fluid source 136 may also be provided. The backup fluid source 136 may have a connector 131 (a male locking luer type, for example) sealed by a cap 147. The sealed fluid circuit assembly 80 may also include a non-reopenable tubing clamp 130 as discussed above. The latter may be provided in an open position such that the tube 110 is open and uncompressed prior to use.

Figure 3:
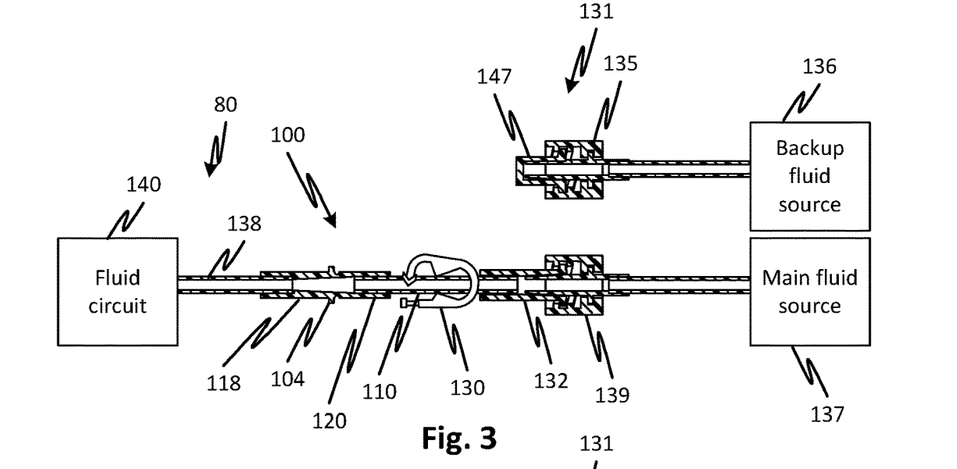
Figure 4:
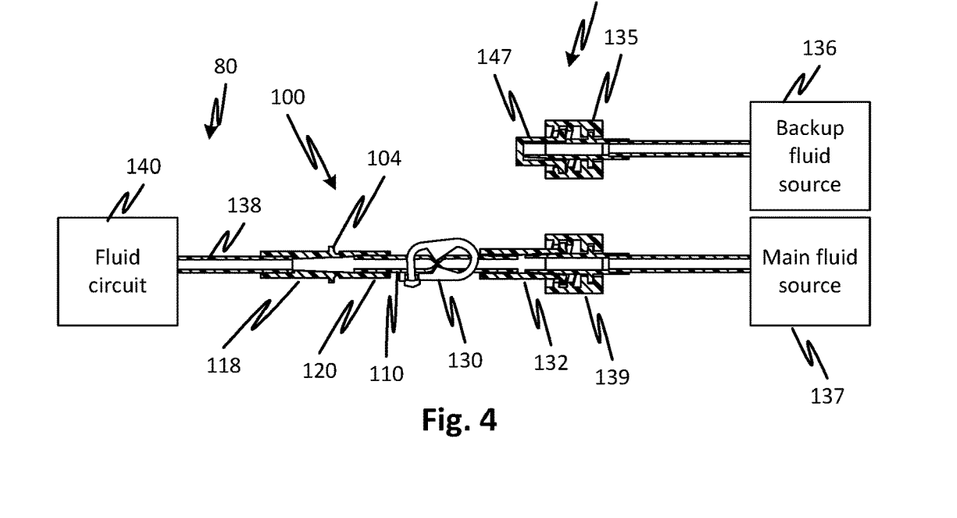
Figure 5:
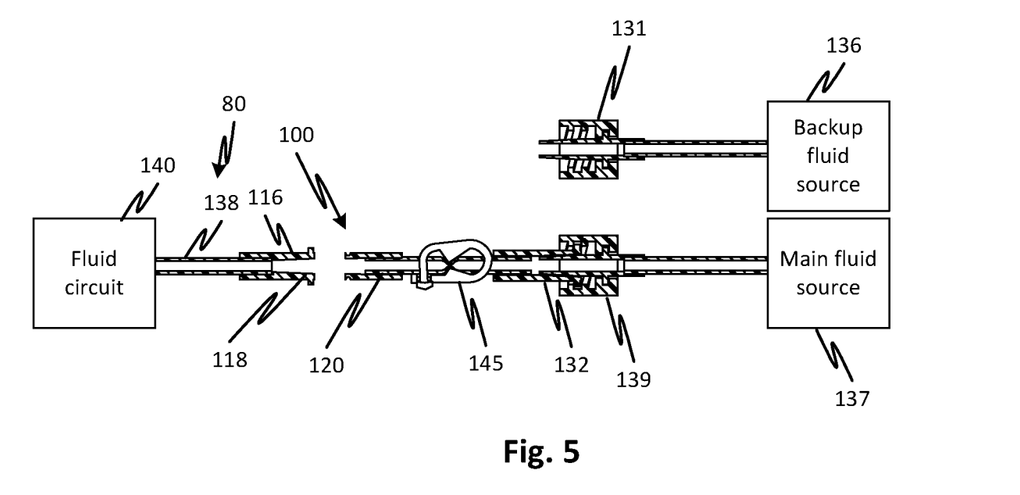
Figure 6:
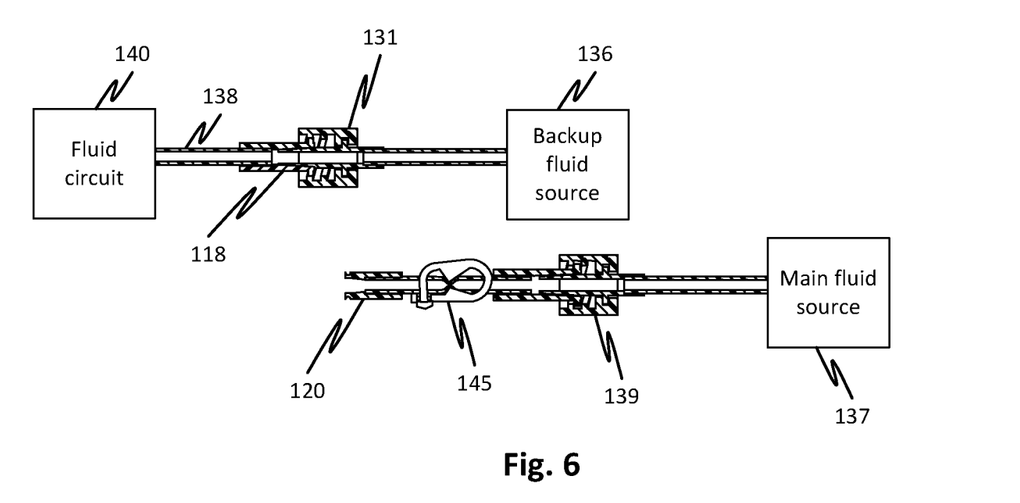

FIGS. 3-6 show stages of use of the components described with reference to the foregoing figures. In FIG. 3, connector 132 and connector 139 are interconnected after removing the respective sealing caps 148 and 147. The main fluid source 137 supplies fluid to the fluid circuit 140 to support a treatment. For example, the main fluid source 137 may flow dialysate continuously to the fluid circuit 140 to support a dialysis treatment. If, during a treatment, the main fluid source 137 become inoperative or otherwise unusable or disfavored as a source of fluid, in order to complete the treatment, an operator may desire to switch to the backup fluid source 136. To do so, in an embodiment, the operator may close the non-reopenable tubing clamp 130 thereby sealing the tube 110 as shown in FIG. 4. Next, as shown in FIG. 5, the frangible connector 100 is fractured at the frangible portion 105. And the connector 116 formed of first side 118 of frangible connector 100 is connected to the connector 131 of the backup fluid source 136 as shown in FIG. 6. The main fluid source 137 remains sealed until the frangible connector 100 second side 120 is removed by disconnecting the connector 139.

Figure 7:
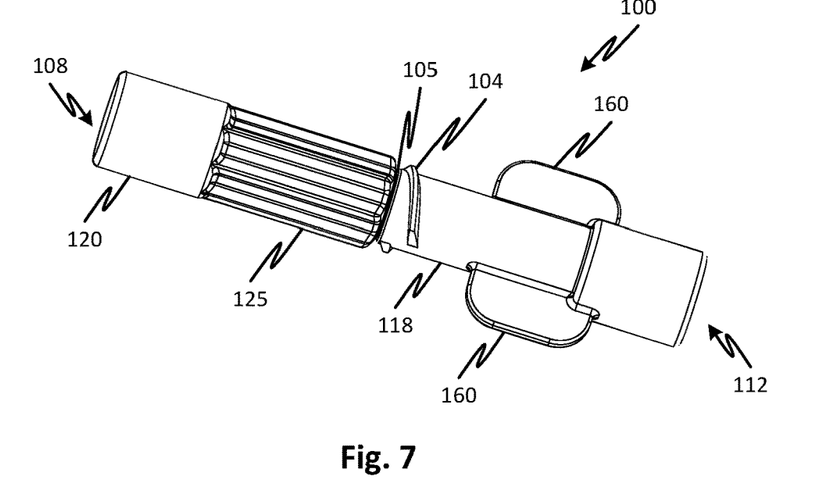
FIGS. 7 and 8 are perspective views of connectors according to the embodiments showing specific features that may be used with any embodiment, including features that help users distinguish the connector parts after fracturing.
Figure 8:
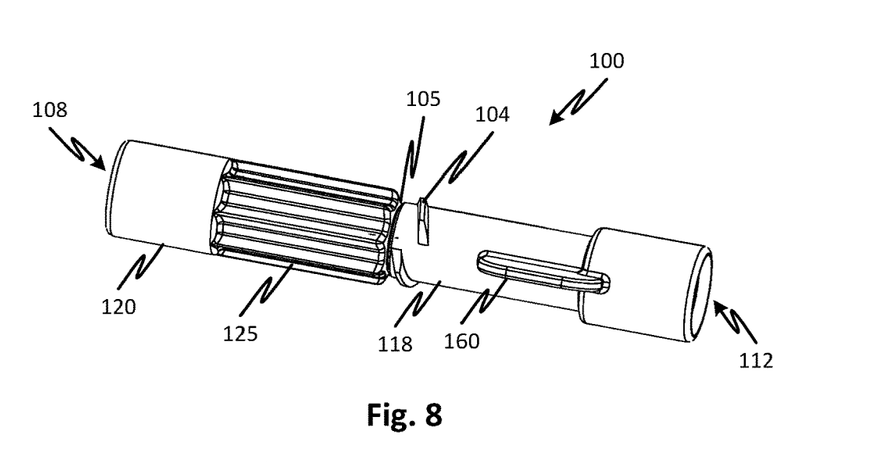
Figure 10:
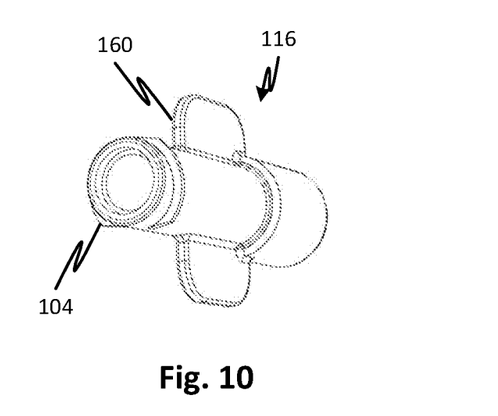
FIG. 10 shows an oblique view of a separated connector according to the embodiment of FIGS. 7 and 8.

Referring to FIGS. 7 and 8, a frangible connector 100 has a first side 118 and second side 120 connected by a frangible portion 105. External threads 104 on the first side 118 form a female luer-type connector 116 when the first 118 and second 120 sides are broken apart at the frangible portion 105. In the present embodiment, distinctive features 125 and 160 help to ensure the connector (first part 118) resulting from separation is easily distinguished from the non-connector (second part 120). In the example shown, a scalloped surface cylindrical surface 125 is formed which can be identified by touch. Wings 160 protrude from the connector which aids in locking the external threads 104 in a locking collar 135 of a mating male luer connector 131. FIG. 10 shows the connector 116 formed from the first part 118 of the FIGS. 7 and 8 embodiments.

Figure 9:
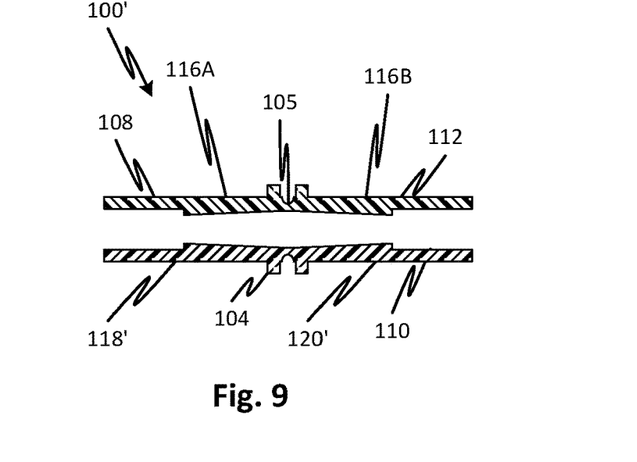
FIG. 9 shows a frangible connection with two sides in which both sides form independent connectors.
Figure 11A:
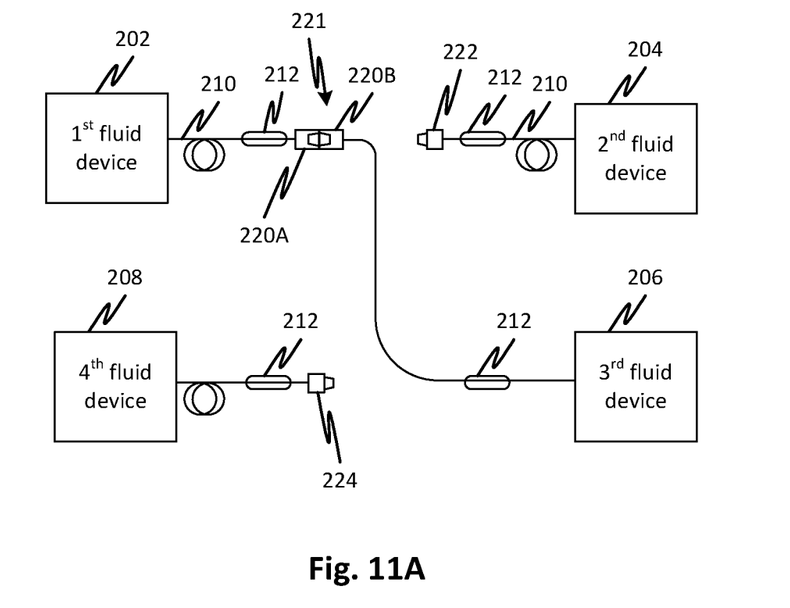
FIGS. 11A and 11B show an embodiment to illustrate devices and methods of a frangible connector device that forms two connectors when fractured.
Figure 11B:
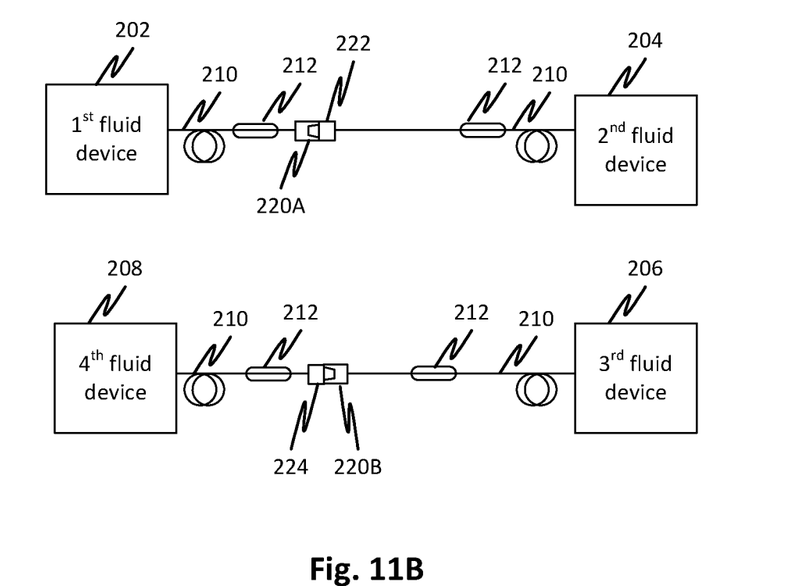

Referring to FIG. 9, as indicated above, a frangible connector 100' can formed such that it splits into two independent connectors 116A and 116B formed by first part 118' and second part 120'. As in the embodiment of FIG. 1A and elsewhere herein, the first and second parts 118' and 120' may be separated by breaking along a frangible portion 105. FIGS. 11A and 11B show an embodiment to illustrate devices and methods of a frangible connector device that forms two connectors when fractured. Referring to FIGS. 11A and 11B, a first fluid device 202 may be a container, a fluid source, a drain, or other supply, conveyance, processing, or consuming device of any type. A second fluid device 204 may be a container, a fluid source, a drain, or other supply, conveyance, processing, or consuming device of any type. A third fluid device 206 may be a container, a fluid source, a drain, or other supply, conveyance, processing, or consuming device of any type. A fourth fluid device 208 may be a container, a fluid source, a drain, or other supply, conveyance, processing, or consuming device of any type. The first fluid device 202 is connected to third fluid device 206 by fluid lines 210 and a frangible connector 221 that can be broken into independent connector 220A and independent connector 22B. The independent connector 220A and independent connector 22B are both illustrated as female connectors but may instead be a combination of male and female connectors. As in the disclosed embodiments, the independent connector 220A and independent connector 220B are joined by a frangible portion to form a continuous lumen in the frangible connector 221 until the frangible portion is broken. Any or all the lines 210 may carry reopenable or non-reopenable clamps 212. The first fluid device 202 may be disconnected from the third fluid device 206 be closing line clamps, breaking the frangible portion of the frangible connector 221. The first fluid device 202 may then be connected to the second fluid device 204 by connecting the independent connector 220A to a connector 222 of the second fluid device 2014 as shown in FIG. 11. In a similar fashion, the independent connector 220B may be connected to a connector 224 of the fourth fluid device 208. It will be observed that a variety of methods may be implemented by combining multiple instances frangible connectors according to the embodiments to make and break connections between fluid devices.

Figure 12:
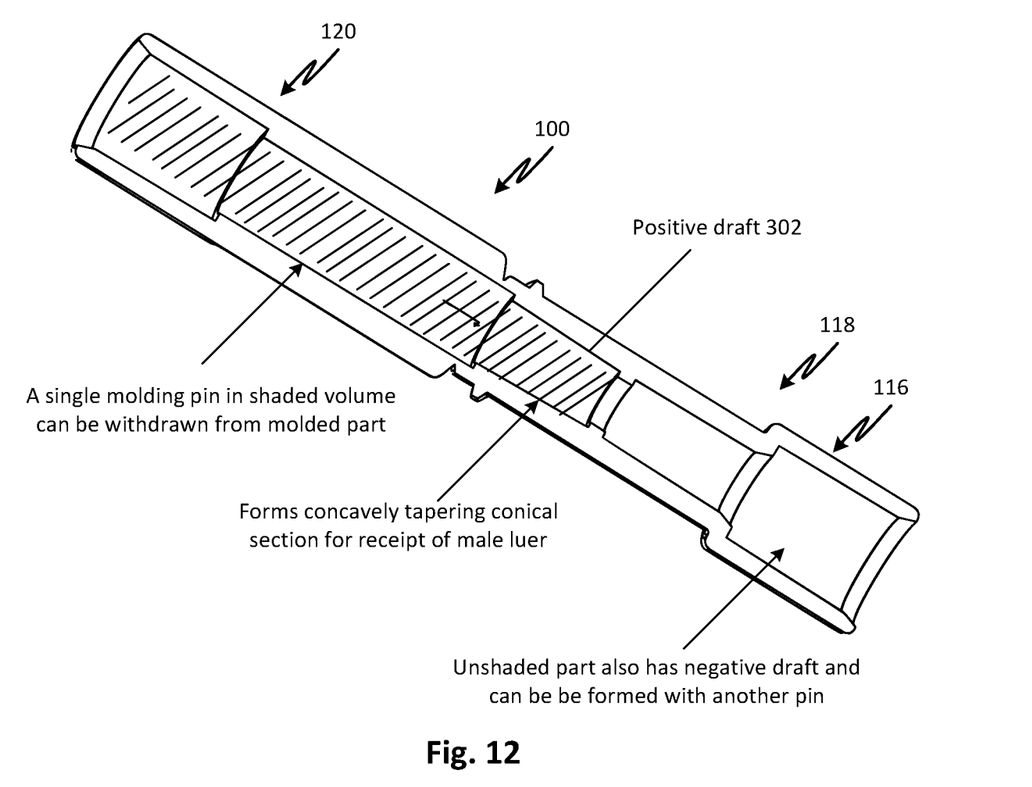
FIG. 12 shows how in the embodiment of FIGS. 11A and 11B and others, the tapered concave conical recess of the female luer can be formed with a single pin having to define a positive draft with another pin opposite, whereby the connector device can be molded in a single operation with two pins and two mold halves.

FIG. 12 shows how in the connector device 100 embodiment of FIGS. 11A and 11B and others, the tapered concave conical recess of the female luer can be formed with a single pin having to define a positive draft with another pin opposite, whereby the connector device can be molded in a single operation with two pins and two mold halves. The shaded volume occupies the second part 120 and a portion of the first part 118 that forms the connector 116. This allows a pin in the shaded volume to be released during molding because the entire shaded volume has a neutral or positive draft. Another pin can be used to fill the unshaded recess. This characteristic may apply to any of the embodiments. Alternatively the parts may be formed by 3D printing and have internal overhangs or other negative draft features.

In all the embodiments, frangible connectors are illustrated in which a continuous lumen allows fluid to flow between two attached connectors or a connector and a non-connector. A frangible portion is provided so that when it is broken the one or two connectors can be separated and attached to one or more other connectors. The frangible portion is formed so as to create a clean and predictable edge of the separated one or two connectors. The connectors and/or non-connectors can have distinctive feature that allow a user to tell them apart easily without looking at them or at least to confirm by touch. Clamps can be reopenable or non-reopenable to achieve release stasis of fluid in connected fluid circuits. Any of the embodiments may be sterile sealed fluid devices including connectors herein. Any of the embodiments may be used for medical fluid handling. Any of the embodiments may be delivered in a sterile package as part of a medical device.

According to first embodiments, the disclosed subject matter includes a connector device that includes an inline fluid channel element. The inline fluid channel element has first and second end portions adapted for bonding to tubing segments. The inline fluid channel element has a middle portion defining a connector attached to the second end portion through a frangible portion that, when fractured, renders the connector operable to connect with a predefined mating connector.

Variations of the first embodiments may be provided to form additional first embodiments in which the connector is of a female locking luer type. Variations of the first embodiments may be provided to form additional first embodiments in which the connector has thread portions. Variations of the first embodiments may be provided to form additional first embodiments in which the connector has an opening shaped to receive the mating connector, a mouth of the opening coinciding with a circular channel defining the frangible portion. Variations of the first embodiments may be provided to form additional first embodiments in which the inline fluid channel is generally cylindrical in shape. Variations of the first embodiments may be provided to form additional first embodiments in which the connector device further includes a fluid circuit for a renal replacement therapy device permanently bonded to the first end portion. Variations of the first embodiments may be provided to form additional first embodiments in which the connector device further includes a releasably capped connector connected to the second end portion. Variations of the first embodiments may be provided to form additional first embodiments in which the releasably capped connector is of a locking luer type. Variations of the first embodiments may be provided to form additional first embodiments in which the second end portion is connected to a tubing segment and with a pre-installed non-reopenable clamp. Variations of the first embodiments may be provided to form additional first embodiments in which the connector device further includes a fluid circuit for a renal replacement therapy device permanently bonded to the first end portion. Variations of the first embodiments may be provided to form additional first embodiments in which the connector device further includes a releasably capped connector connected to the second end portion. Variations of the first embodiments may be provided to form additional first embodiments in which the releasably capped connector is of a locking luer type.

According to second embodiments, the disclosed subject matter includes a method of supplying fluid for a renal replacement therapy. The method includes connecting fluid circuit of a renal replacement therapy device to a first source of fluid by a fluid channel element. The method includes supplying fluid from the source to begin a therapeutic treatment. The method includes halting the supply of fluid from the source prior to completing the treatment. The method includes fracturing the fluid channel element to form a connector. The method includes connecting the connector to a second source of fluid and continuing the treatment.

Variations of the second embodiments may be provided to form additional second embodiments in which the method includes, after halting said supply of fluid, clamping a tube that connects the first source of fluid to the fluid channel element. Variations of the second embodiments may be provided to form additional second embodiments in which the method includes, after halting said supply of fluid, clamping a tube that connects the first source of fluid to the fluid channel element using a non-reopenable clamp. Variations of the second embodiments may be provided to form additional second embodiments in which the method includes, after halting said supply of fluid, clamping a tube that connects the first source of fluid to the fluid channel element using a non-reopenable clamp and leaving a portion of the fluid channel element on a connector of the first fluid source to keep it sealed from the external environment. Variations of the second embodiments may be provided to form additional second embodiments in which the fracturing is effective to define and render accessible the mouth of an opening of the connector. Variations of the second embodiments may be provided to form additional second embodiments in which the connector is of female luer type connector. Variations of the second embodiments may be provided to form additional second embodiments in which the fluid channel element is a generally cylindrical plastic part. Variations of the second embodiments may be provided to form additional second embodiments in which the fracturing includes fracturing at a circular score line on the generally cylindrical plastic part.

According to third embodiments, the disclosed subject matter includes a connector device that includes an inline fluid channel element. The inline fluid channel element has first and second end portions adapted for bonding to tubing segments. The inline fluid channel element has a middle portion defining a connector attached to the second end portion through a frangible portion that, when fractured, renders the connector to remain attached to the first portion and operable to connect with a predefined mating connector and also renders the second portion unusable as a connector thereby preventing connection to an external fluid circuit.

Variations of the third embodiments may be provided to form additional third embodiments in which the connector is of a female locking luer type. Variations of the third embodiments may be provided to form additional third embodiments in which the connector has thread portions. Variations of the third embodiments may be provided to form additional third embodiments in which the connector has an opening shaped to receive the mating connector, a mouth of the opening coinciding with a circular channel defining the frangible portion. Variations of the third embodiments may be provided to form additional third embodiments in which the inline fluid channel is generally cylindrical in shape. Variations of the third embodiments may be provided to form additional third embodiments in which the connect device further includes a fluid circuit for a renal replacement therapy device permanently bonded to the first end portion. Variations of the third embodiments may be provided to form additional third embodiments in which the connect device further includes a releasably capped connector connected to the second end portion. Variations of the third embodiments may be provided to form additional third embodiments in which the releasably capped connector is of a locking luer type. Variations of the third embodiments may be provided to form additional third embodiments in which the second end portion is connected to a tubing segment and with a pre-installed non-reopenable clamp. Variations of the third embodiments may be provided to form additional third embodiments in which the connect device further includes a fluid circuit for a renal replacement therapy device permanently bonded to the first end portion. Variations of the third embodiments may be provided to form additional third embodiments in which the connect device further includes a releasably capped connector connected to the second end portion. Variations of the third embodiments may be provided to form additional third embodiments in which the releasably capped connector is of a locking luer type.

According to fourth embodiments, the disclosed subject matter includes a connector device that includes an inline fluid channel element. The inline fluid channel element has first and second end portions adapted for bonding to tubing segments. The inline fluid channel element has a middle portion defining a connector attached to the second end portion through a frangible portion that, when fractured, renders the connector operable to connect with a predefined mating connector. Variations of the third embodiments may be provided to form additional third embodiments in which the connector is of a female locking luer type.

Variations of the fourth embodiments may be provided to form additional fourth embodiments in which the connector has thread portions. Variations of the fourth embodiments may be provided to form additional fourth embodiments in which the connector has an opening shaped to receive the mating connector, a mouth of the opening coinciding with a circular channel defining the frangible portion. Variations of the fourth embodiments may be provided to form additional fourth embodiments in which the inline fluid channel is generally cylindrical in shape. Variations of the fourth embodiments may be provided to form additional fourth embodiments in which the connector device further includes a fluid circuit for a renal replacement therapy device permanently bonded to the first end portion. Variations of the fourth embodiments may be provided to form additional fourth embodiments in which the connector device further includes a releasably capped connector connected to the second end portion. Variations of the fourth embodiments may be provided to form additional fourth embodiments in which the releasably capped connector is of a locking luer type. Variations of the fourth embodiments may be provided to form additional fourth embodiments in which the second end portion is connected to a tubing segment with a flow sealing element that prevents flow through the second end portion. Variations of the fourth embodiments may be provided to form additional fourth embodiments in which the connector device further includes a fluid circuit for a renal replacement therapy device permanently bonded to the first end portion. Variations of the fourth embodiments may be provided to form additional fourth embodiments in which the connector device further includes a releasably capped connector connected to the second end portion. Variations of the fourth embodiments may be provided to form additional fourth embodiments in which the releasably capped connector is of a locking luer type.

According to fifth embodiments, the disclosed subject matter includes a method of supplying fluid for a renal replacement therapy. The method includes connecting fluid circuit of a renal replacement therapy device to a first source of fluid by a fluid channel element. The method includes supplying fluid from the source. The method includes halting the supply of fluid from the source after a predetermined time. The method includes fracturing the fluid channel element to form a connector. The method includes connecting the connector to a second source of fluid and continuing the supplying.

Variations of the fifth embodiments may be provided to form additional fifth embodiments in which the method further includes, after halting said supply of fluid, clamping a tube that connects the first source of fluid to the fluid channel element. Variations of the fifth embodiments may be provided to form additional fifth embodiments in which the method further includes, after halting said supply of fluid, sealing a tube that connects the first source of fluid to the fluid channel element to prevent flow therethrough. Variations of the fifth embodiments may be provided to form additional fifth embodiments in which the method further includes, after halting said supply of fluid, sealing off flow through a tube that connects the first source of fluid to the fluid channel element and leaving a portion of the fluid channel element on a connector of the first fluid source to keep it sealed from the external environment. Variations of the fifth embodiments may be provided to form additional fifth embodiments in which the fracturing is effective to define and render accessible the mouth of an opening of the connector. Variations of the fifth embodiments may be provided to form additional fifth embodiments in which the connector is of female luer type connector. Variations of the fifth embodiments may be provided to form additional fifth embodiments in which the fluid channel element is a generally cylindrical plastic part. Variations of the fifth embodiments may be provided to form additional fifth embodiments in which the fracturing includes fracturing at a circular score line on the generally cylindrical plastic part.

According to embodiments, the disclosed subject matter includes a connector device. An inline fluid channel element has first and second end portions adapted for bonding to tubing segments. The inline fluid channel element connector has a middle portion defining a connector attached to the second end portion through a frangible portion that when fractured renders the connector operable to connect with a predefined mating connector.

Variants of the foregoing may be such that the connector is of a female locking luer type. Variants of the foregoing may be such that the connector has thread portions. Variants of the foregoing may be such that the connector has an opening shaped to receive the mating connector, a mouth of the opening coinciding with a circular channel defining the frangible portion. Variants of the foregoing may be such that the inline fluid channel is generally cylindrical in shape. Variants of the foregoing may include a fluid circuit for a renal replacement therapy device permanently bonded to the first end portion. Variants of the foregoing may include a releasably capped connector connected to the second end portion. Variants of the foregoing may be such that the releasably capped connector is of a locking luer type. Variants of the foregoing may be such that the second end portion is connected to a tubing segment and with a pre-installed non-reopenable clamp. Variants of the foregoing may include a fluid circuit for a renal replacement therapy device permanently bonded to the first end portion. Variants of the foregoing may include a releasably capped connector connected to the second end portion. Variants of the foregoing may be such that the releasably capped connector is of a locking luer type.

According to embodiments, the disclosed subject matter includes a method of supplying fluid for a renal replacement therapy. The method includes connecting fluid circuit of a renal replacement therapy device to a first source of fluid by a fluid channel element. The method includes supplying fluid from the source to begin a therapeutic treatment. The method includes halting the supply of fluid from the source prior to completing the treatment. The method includes fracturing the fluid channel element to form a connector. The method includes connecting the connector to a second source of fluid and continuing the treatment.

Variants of the foregoing may include after halting the supply of fluid, clamping a tube that connects the first source of fluid to the fluid channel element. Variants of the foregoing may include, after halting the supply of fluid, clamping a tube that connects the first source of fluid to the fluid channel element using a non-reopenable clamp. Variants of the foregoing may include, after halting the supply of fluid, clamping a tube that connects the first source of fluid to the fluid channel element using a non-reopenable clamp and leaving a portion of the fluid channel element on a connector of the first fluid source to keep it sealed from the external environment. Variants of the foregoing may be such that the fracturing is effective to define and render accessible the mouth of an opening of the connector. Variants of the foregoing may be such that the connector is of female luer type connector. Variants of the foregoing may be such that the fluid channel element is a generally cylindrical plastic part. Variants of the foregoing may be such that the fracturing includes fracturing at a circular score line on the generally cylindrical plastic part.

According to sixth embodiments, the disclosed subject matter includes a connector device. A fluid channel element is connected at a first end to a first fluid device and at a second end to a second fluid device permitting fluid to flow between the first and second fluid devices. The first and second fluid devices each include any, or a combination of, a fluid circuit, a fluid cartridge, a fluid consumer, a fluid supply, a sterile sealed cap, a drain, a tubing extension, a fluid conveyance, or a fluid store. The fluid channel element is generally elongate and having first and second parts, each with one of the first and second ends, that are integral and joined by a frangible portion that forms a smooth edge when fractured to separate the first and second parts. At least one of the first and second parts is shaped such that it is rendered a connector connectable by sealing and locking to a predefined connector.

In variants thereof, the sixth embodiments include some in which the first and second ends are bonded, respectively, to the first and second fluid devices. In variants thereof, the sixth embodiments include some in which the at least one of the first and second parts is the first part. In variants thereof, the sixth embodiments include some in which the first part has extensions protruding therefrom and the second part does not. In variants thereof, the sixth embodiments include some in which the second part has a textured surface that is different from the surface of the first part. In variants thereof, the sixth embodiments include some in which the first and second parts have different surface textures so that they can be discriminated tactilely by a user. In variants thereof, the sixth embodiments include some in which the at least one of the first and second parts is both the first and second part.

According to the seventh embodiments, the disclosed subject matter includes a connector device with a fluid channel element that has an internal lumen to permit fluid to flow between first and second ends of the element. The fluid channel element is generally elongate and having first and second parts, each terminating at a respective one of first and second ends, the parts is integral and joined by a frangible portion that forms a smooth edge when fractured to separate the first and second parts. At least one of the first and second parts is shaped such that it is rendered a connector connectable by sealing and locking to a predefined connector.

In variants thereof, the seventh embodiments include some in which the first and second ends are bonded, respectively, to the first and second fluid devices. In variants thereof, the seventh embodiments include some in which the at least one of the first and second parts is the first part. In variants thereof, the seventh embodiments include some in which the first part has extensions protruding therefrom and the second part does not. In variants thereof, the seventh embodiments include some in which the second part has a textured surface that is different from the surface of the first part. In variants thereof, the seventh embodiments include some in which the first and second parts have different surface textures so that they can be discriminated tactilely by a user. In variants thereof, the seventh embodiments include some in which the at least one of the first and second parts is both the first and second part.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, dialysate methods, devices, and systems. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A method of supplying a fluid for a renal replacement therapy, comprising:
providing a fluid circuit that is fluidly connected by a first tube to a fluid channel element that has a first end and an opposite second end, the first end connected to the first tube and the second end connected to a second tube that extends to a first connector closed with a cap;
removing the cap from the first connector;
connecting the first connector to a luer-type connector on a first source of the fluid to create a fluid connection from the first source through the fluid channel element to the fluid circuit;
supplying the fluid from the first source of the fluid to begin a therapeutic treatment, the supplying including flowing the fluid through the fluid channel element in a flow direction from the second end to the first end;
halting the supplying of the fluid from the first source prior to completing the therapeutic treatment;
fracturing the fluid channel element between the first end and the second end to form a second connector attached to the first end of the fluid channel element and to physically separate the second end from the first end;
connecting the second connector to a luer-type connector on a second source of the fluid;
flowing the fluid from the second source through the second connector in said flow direction; and
continuing the therapeutic treatment with the fluid from the second source, wherein
the first connector and the second connector are physically configured to mate with a same luer-type connector.

2. The method of claim 1, further comprising, after halting said supplying of the fluid, clamping a tube that connects the first source of the fluid to the fluid channel element.

3. The method of claim 1, further comprising, after halting said supplying of the fluid, clamping a tube that connects the first source of the fluid to the fluid channel element using a non-reopenable clamp.

4. The method of claim 1, further comprising, after halting said supplying of the fluid, clamping a tube that connects the first source of the fluid to the fluid channel element using a non-reopenable clamp and leaving the second end of the fluid channel element connected by the first connector to the first source of the fluid to keep the first source sealed from an external environment.

5. The method of claim 1, wherein the fracturing is effective to define and render accessible a mouth of an opening of the second connector.

6. The method of claim 5, wherein the second connector is female luer type connector.

7. The method of claim 1, wherein the fluid channel element is a generally cylindrical plastic part.

8. The method of claim 7, wherein the fracturing includes fracturing at a circular score line on the generally cylindrical plastic part.

* * * * *